United States Patent
Treleaven et al.

(10) Patent No.: US 10,597,345 B2
(45) Date of Patent: Mar. 24, 2020

(54) METHODS OF INHIBITING POLYMERIZATION OF VINYL AROMATIC MONOMERS

(71) Applicant: Chevron Phillips Chemical Company LP, The Woodlands, TX (US)

(72) Inventors: William D. Treleaven, Porter, TX (US); Maruti Bhandarkar, Kingwood, TX (US); Stephen L. Kelly, Kingwood, TX (US); Wei Wang, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/968,911

(22) Filed: May 2, 2018

(65) Prior Publication Data

US 2019/0337877 A1 Nov. 7, 2019

(51) Int. Cl.
- *C07C 37/74* (2006.01)
- *C07C 7/04* (2006.01)
- *C07C 7/20* (2006.01)

(52) U.S. Cl.
CPC .............. *C07C 37/74* (2013.01); *C07C 7/04* (2013.01); *C07C 7/20* (2013.01)

(58) Field of Classification Search
CPC ...................................................... C07C 37/74
See application file for complete search history.

(56) References Cited

U.S. PATENT DOCUMENTS

| | | |
|---|---|---|
| 4,468,343 A | 8/1984 | Butler et al. |
| 5,954,924 A | 9/1999 | Art |
| 6,348,136 B1 | 2/2002 | Ledoux et al. |
| 6,620,969 B1 * | 9/2003 | Nishimura ............. B01D 3/322 165/133 |
| 6,863,779 B2 | 3/2005 | Schmaus et al. |
| 2002/0040845 A1 * | 4/2002 | Schmaus ................... C07C 7/05 203/49 |
| 2004/0019247 A1 | 1/2004 | Mitulla et al. |

OTHER PUBLICATIONS

"Styrene Monomer: Environmental, Health & Safety Guidelines", Section 2.4.3—Standard Inhibitor Levels, CEFIC, pp. 1-2, Jul. 22, 2016.

* cited by examiner

*Primary Examiner* — Brian A Mccaig
(74) *Attorney, Agent, or Firm* — Eversheds Sutherland (US) LLP

(57) ABSTRACT

Provided herein are methods of inhibiting polymerization of vinyl aromatic monomers. The methods include distilling a vinyl aromatic monomer in a distillation column to form a vinyl aromatic monomer distillate; removing the vinyl aromatic monomer distillate from the distillation column; combining the vinyl aromatic monomer distillate with 4-tert-butylcatechol (TBC) to form a treated distillate; and adding a reflux liquid that includes the treated distillate to the distillation column liquid of the distillation column. An added oxygen gas may be present in a distillation column liquid in an amount of at least 1 ppmw, based on the weight of the vinyl aromatic monomer.

20 Claims, 1 Drawing Sheet

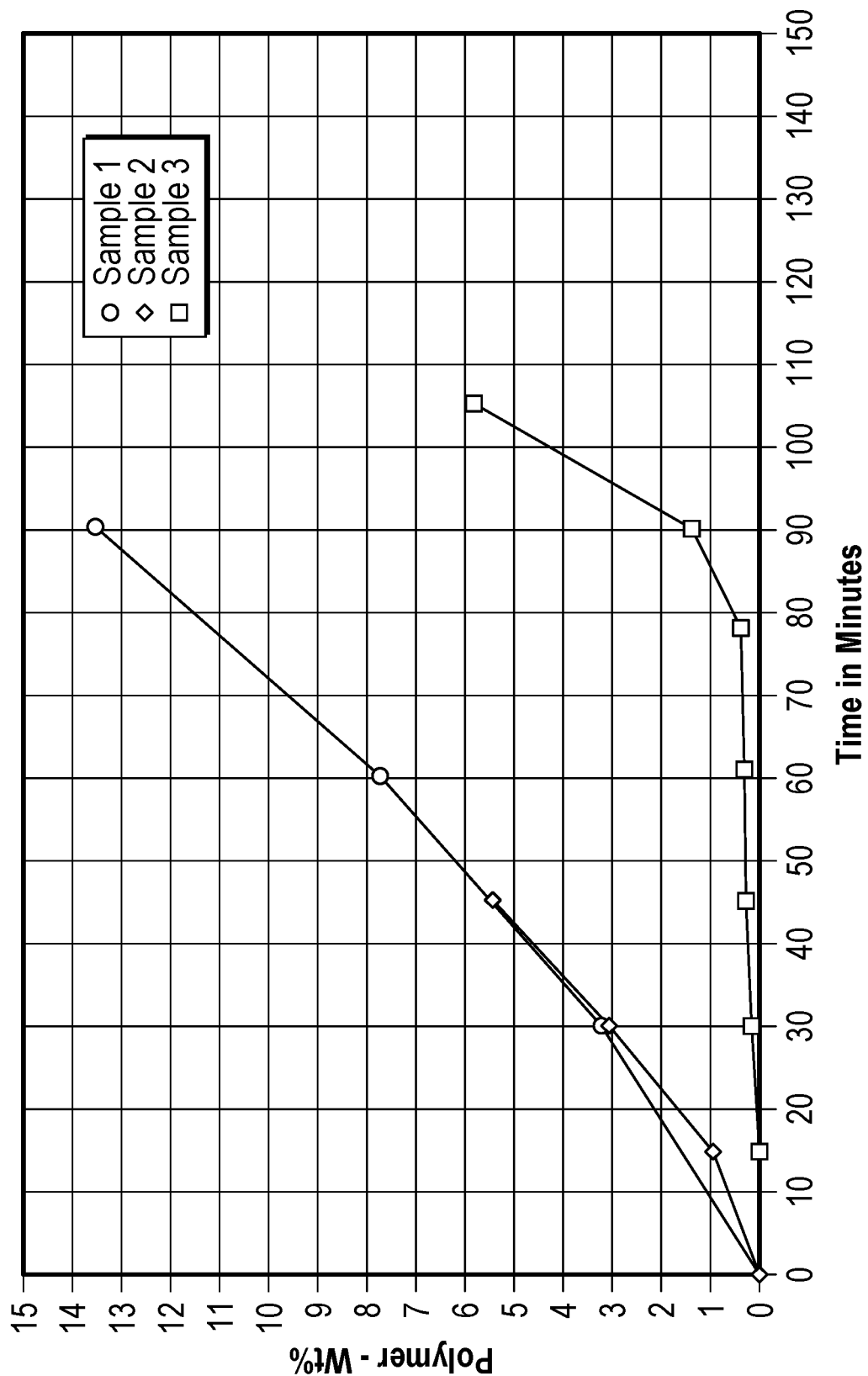

METHODS OF INHIBITING POLYMERIZATION OF VINYL AROMATIC MONOMERS

FIELD OF THE INVENTION

The present disclosure is directed to methods of inhibiting polymerization of vinyl aromatic monomers, such as styrene.

BACKGROUND

Many commercial products are made from styrene and other polymerized vinyl aromatic monomers. Vinyl aromatic monomers, such as styrene, may autopolymerize, which can be undesirable when operating a monomer production unit. In a typical styrene production unit, a distillation is performed to separate styrene from other compounds, such as ethyl benzene. When polymerization of styrene occurs while operating a styrene production unit, styrene product may be lost and/or the styrene production unit may become inoperable, typically due to plugging caused by polystyrene.

Due, at least in part, to the fact that the autopolymerization of styrene is accelerated by heat, the distillation of styrene and other vinyl aromatic monomers usually is performed at reduced temperatures and low pressures (vacuum), typically at a pressure and temperature that is as low as possible.

In addition to these distillation parameters, 4-tert-butylcatechol (TBC) has been added to product styrene to prevent or minimize polymerization during transport of the product styrene to a polystyrene production unit. Some of the TBC added to the styrene product can be recycled to the styrene product distillation column through the reflux, but this TBC is usually ineffective due a lack of oxygen in the low pressure (vacuum) distillation columns. As a result, TBC typically exits with the tars stream and is burned as waste.

Methods of inhibiting polymerization of styrene and other vinyl aromatic monomers that reduce the amount of TBC used as an inhibitor and/or increase the effectiveness of TBC as an inhibitor, especially in a distillation column, are desired.

BRIEF SUMMARY

Provided herein are methods of inhibiting polymerization of vinyl aromatic monomers. In embodiments, the methods comprise [1] distilling a vinyl aromatic monomer in a distillation column to form a vinyl aromatic monomer distillate, the distillation column including a distillation column liquid; [2] removing the vinyl aromatic monomer distillate from the distillation column; [3] combining the vinyl aromatic monomer distillate with 4-tert-butylcatechol (TBC) to form a treated distillate; and [4] adding a reflux liquid comprising the treated distillate to the distillation column liquid of the distillation column; wherein an added oxygen gas is present in the distillation column liquid in an amount of at least 1 ppmw, based on the weight of the vinyl aromatic monomer. In one embodiment, the methods further comprise forming a vinyl aromatic monomer product and the reflux liquid from the treated distillate; directing the reflux liquid into the distillation column; and directing the vinyl aromatic monomer product to storage. The vinyl aromatic monomer distillate may comprise TBC. In particular embodiments, the added oxygen gas is present in the distillation column liquid in an amount of at least 5 ppmw, or about 5 ppmw. Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

BRIEF DESCRIPTION OF THE DRAWINGS

The following FIGURES form part of the present specification and are included to further demonstrate certain aspects of the present invention. The invention may be better understood by reference to one or more of these FIGURES in combination with the detailed description of specific embodiments presented herein.

FIG. 1 depicts the weight percentage of polystyrene that formed in three test samples upon heating at 120° C.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain terms are used throughout the following description and claims to refer to particular features or components. As one skilled in the art will appreciate, different persons may refer to the same feature or component by different names. This document does not intend to exhaustively distinguish between components or features that differ in name but not structure or function.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

In the following discussion and in the claims, the terms "includes," "is," "containing," "having," "characterized by," and "comprises" are used in an open-ended fashion, and thus should be interpreted to mean "including, but not limited to." When systems and methods are claimed or described in terms of "comprising" various components or steps, the systems and methods can also "consist essentially of" or "consist of" the various components or steps, unless stated otherwise.

The terms "a," "an," and "the" are intended to include plural alternatives, e.g., at least one. For instance, the disclosure of "a feedstock," "a compound," "a catalyst," and the like, is meant to encompass one, or mixtures or combinations of more than one feedstock, compound, catalyst, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in an aspect of the invention, that the distilling occurs at a temperature of 75° C. to 105° C. This range should be interpreted as encompassing temperatures in a range from "about" 75° C. to "about" 105° C., and further encompass each of 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., and 105° C., including any ranges and sub-ranges between any of these values.

Applicant reserves the right to proviso out or exclude any individual members of any such group, including any sub-ranges or combinations of sub-ranges within the group, that can be claimed according to a range or in any similar manner, if for any reason Applicant chooses to claim less than the full measure of the disclosure, for example, to account for a reference that Applicant can be unaware of at the time of the filing of the application. Further, Applicant reserves the right to proviso out or exclude any individual substituents, groups, analogs, compounds, ligands, structures, pressures, temperatures, and the like, or any members of a claimed genus or subgenus, if for any reason Applicant chooses to claim less than the full measure of the disclosure, for example, to account for a reference that Applicant can be unaware of at the time of the filing of the application.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The following discussion is directed to various aspects or embodiments of the invention. The figures are not necessarily to scale, therefore, certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

As used herein, "about" is meant to account for variations due to experimental error. All numerical measurements are understood to be modified by the word "about", whether or not "about" is explicitly recited, unless specifically stated otherwise. Thus, for example, the statement "production of 10,000 tonnes," is understood to mean "production of about 10,000 tonnes."

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified.

Provided herein are methods that may ensure or increase the effectiveness of TBC as a polymerization inhibitor, especially in a distillation column. This advantage may be achieved by the presence of an added oxygen gas in the distillation columns provided herein. The added oxygen gas may ensure or increase the activity of TBC, which may be added to a stream at the top of the distillation columns provided herein. A portion of the TBC added to the stream at the top of the distillation column may be refluxed back into the distillation column, where the added oxygen gas can ensure or increase the polymerization inhibition activity of the TBC. As a result, the methods provided herein may (i) reduce the amount of TBC needed to achieve a desired level of polymerization inhibition, thereby reducing costs, and/or (ii) increase the efficiency of the TBC as a polymerization inhibitor, especially in a distillation column.

Provided herein are methods of inhibiting polymerization of vinyl aromatic monomers. In one embodiment, the methods comprise distilling a vinyl aromatic monomer in a distillation column to form a vinyl aromatic monomer distillate, the distillation column including a distillation column liquid; removing the vinyl aromatic monomer distillate from the distillation column; combining the vinyl aromatic monomer distillate with 4-tert-butylcatechol (TBC) to form a treated distillate; and adding a reflux liquid comprising the treated distillate to the distillation column liquid of the distillation column; wherein an added oxygen gas is present in the distillation column liquid in an amount of at least 1 ppmw, based on the weight of the vinyl aromatic monomer. In a particular embodiment, the methods further comprise forming a vinyl aromatic monomer product and the reflux liquid from the treated distillate; directing the reflux liquid into the distillation column; and directing the vinyl aromatic monomer product to storage. The vinyl aromatic monomer distillate may comprise TBC. In addition to TBC, the methods provided herein may include the use of another polymerization inhibitor or polymerization retardant, such as 4,6-dinitro-2-sec-butyl phenol (DNBP).

Distillation Column Apparatus

Generally, any distillation column apparatus known in the art may be used to perform the methods provided herein. Typically, a distillation column hosts countercurrent flows of vapor and liquid phases. The contact between these two phases may be increased and/or maximized by including trays and/or packing in the distillation column. The distillation column apparatus also may comprise at least one of a reboiler and a condenser. The condenser may be connected to the distillation column by a pipe that exits the top of the distillation column or a portion near the top of the distillation column, and TBC may be added via an inlet in the pipe. The inlet may be located downstream of a downturn in the pipe.

In one embodiment, the distillation column comprises a boot. The boot may include one or more inlets—for example, three inlets—that may permit gasses to be introduced to the distillation column. At least one of the one or more inlets may be connected to an air purge, and the remaining inlets may be connected to a gas purge. The gas purge may be an inert gas purge, or the gas purge may comprise an inert gas and oxygen gas. In a particular embodiment, the distillation column comprises a boot having three inlets, and two of the three inlets are connected to a gas purge, such as a nitrogen gas purge, and one of the three inlets is connected to an air purge. Other combinations are envisioned.

Oxygen Gas

The polymerization inhibition activity of TBC in a distillation column may be ensured, increased, and/or maximized by the presence of oxygen gas in the distillation column, including the distillation column liquid. In embodiments, the added oxygen gas of the methods provided herein is present in the distillation column liquid in an amount of at least 5 ppmw; about 5 ppmw; about 1 ppmw to about 100 ppmw; about 1 ppmw to about 75 ppmw; about 1 ppmw to about 50 ppmw; about 1 ppmw to about 20 ppmw; about 1 ppmw to about 15 ppmw; about 1 ppmw to about 10 ppmw; about 5 ppmw to about 100 ppmw; about 5 ppmw to about 75 ppmw; about 5 ppmw to about 50 ppmw; about 5 ppmw to about 20 ppmw; about 5 ppmw to about 15 ppmw; or about 5 ppmw to about 10 ppmw. The concentration of oxygen gas in the distillation column may be measured by any means known in the art. For example, a HACH® Orbisphere A1100 dissolved oxygen sensor (HACH® LANGE GmbH, Dusseldorf, Germany) may be used for this application.

In embodiments, a concentration gradient of the added oxygen gas exists in the distillation column. For example, a concentration of the added oxygen gas in the vinyl aromatic monomer of the distillation column liquid may be greater than a concentration of the added oxygen gas in the vinyl aromatic monomer distillate. As a further example, a concentration of the added oxygen gas in a bottom portion of the distillation column may be greater than a concentration of the added oxygen gas in a top portion of the distillation column. The "bottom portion of the distillation column" and the "top portion of the distillation column" may be determined by dividing the height of a distillation column by 2, the height being the distance from the top of the distillation column to the bottom of the distillation column. The bottom of the distillation column may be the bottom of the distillation column's boot, if applicable.

Not wishing to be bound by any particular theory, it is believed that the foregoing concentration gradient of the added oxygen gas in the distillation column may be beneficial because it may ensure that the effectiveness of TBC as a polymerization inhibitor is greatest at the bottom portion of the column or in the distillation column liquid, which is where the polymerization of the vinyl aromatic monomer may be more likely to [1] occur due to the relatively higher temperatures, and/or [2] plug the inlets or piping connected to the bottom portion or boot of the distillation column.

At least a portion of the added oxygen gas of the methods herein may be introduced to the distillation column via an air purge, a gas purge, or a combination thereof. Therefore, in embodiments, the methods provided herein further comprise adding at least one of air and gas to the distillation column with an air purge and/or gas purge, respectively. The air purge, gas purge, or a combination thereof may add air to the distillation column at a rate sufficient to maintain at least 1 ppmw, at least 5 ppmw, or about 5 ppmw of added oxygen gas in the distillation column liquid. The gas purge may add a gas comprising oxygen gas and at least one inert gas, such as nitrogen, argon, or a combination thereof. The air purge and/or gas purge may add the air and/or gas, respectively, to a bottom portion of the distillation column. In embodiments, the distillation column comprises a boot, and the air purge and/or gas purge is connected to the boot.

Distillation Temperatures/Pressures

The methods provided herein generally may be performed at any temperature and/or pressure that permits the production of a vinyl aromatic monomer product. Not wishing to be bound by any particular theory, it is believed that the presence of the added oxygen gas in the distillation column ensures the activity of the TBC, thereby permitting the distillations of the methods provided herein to be performed at temperatures and/or pressures higher than those used in low temperature and low pressure processes designed to minimize or prevent monomer polymerization.

In embodiments, the distilling of the methods provided herein occurs at a temperature of about 50° C. to about 130° C.; about 70° C. to about 110° C.; about 75° C. to about 105° C.; or about 77° C. to about 101° C.

In embodiments, a temperature gradient exists in the distillation column. In one embodiment, an internal temperature (° C.) of a top portion of the distillation column is about 10% to about 40% less than or about 20% to about 30% less than an internal temperature (° C.) of a bottom portion of the distillation column. For example, if the internal temperature of a top portion of the distillation column is 90° C. and 20% less than the internal temperature of a bottom portion of the distillation column, then the internal temperature of the bottom portion of the distillation column would be 112.5° C. In another embodiment, an internal temperature of a top portion of the distillation column is about 70° C. to about 85° C., and an internal temperature of a bottom portion of the distillation column is about 90° C. to about 110° C. In a still further embodiment, an internal temperature of a top portion of the distillation column is about 75° C. to about 80° C., and an internal temperature of a bottom portion of the distillation column is about 95° C. to about 105° C. In yet another embodiment, an internal temperature of a top portion of the distillation column is about 77° C., and an internal temperature of a bottom portion of the distillation column is about 101° C.

In embodiments, the distilling occurs at a pressure of about 70 mm Hg to about 120 mm Hg; or about 80 mm Hg to about 110 mm Hg. In one embodiment, a pressure gradient exists in the distillation column. In embodiments, a pressure gradient exists in the distillation column. In one embodiment, a pressure at a top portion of the distillation column is about 10% to about 40% less than or about 20% to about 30% less than a pressure at a bottom portion of the distillation column. For example, if the pressure of a top portion of the distillation column is 85 mm Hg and 20% less than the pressure of a bottom portion of the distillation column, then the pressure of the bottom portion of the distillation column would be 106.25 mm Hg. In a particular embodiment, the pressure at a top portion of the distillation column is 80 mm Hg, and the pressure at a bottom portion of the distillation column is 110 mm Hg.

In one embodiment, the distilling occurs at a temperature of about 50° C. to about 130° C. and at a pressure of about 70 mm Hg to about 120 mm Hg. In another embodiment, the distilling occurs at a temperature of about 50° C. to about 130° C. and at a pressure of about 80 mm Hg to about 110 mm Hg. In a further embodiment, the distilling occurs at a temperature of about 70° C. to about 110° C. and at a pressure of about 70 mm Hg to about 120 mm Hg. In yet another embodiment, the distilling occurs at a temperature of about 70° C. to about 110° C. and at a pressure of about 80 mm Hg to about 110 mm Hg. In a still further embodiment, the distilling occurs at a temperature of about 75° C. to about 105° C. and at a pressure of about 70 mm Hg to about 120 mm Hg. In an additional embodiment, the distilling occurs at a temperature of about 75° C. to about 105° C. and at a pressure of about 80 mm Hg to about 110 mm Hg. Further embodiments are provided in Table 1, which provides the distillation temperature range, temperature gradient range, distillation pressure range, and pressure gradient range for each embodiment. A "temperature gradient range" in Table 1 of "10-40" or "20-30" indicates that the internal temperature at a top portion of the distillation column is about 10% to about 40% less than an internal temperature at a bottom portion of the distillation column, or about 20% to about 30% less than an internal temperature at a bottom portion of the distillation column. Similarly, a "pressure gradient range" in the following table of "10-40" or "20-30" indicates that the pressure at a top portion of the distillation column is about 10% to about 40% less than a pressure at a bottom portion of the distillation column, or about 20% to about 30% less than a pressure at a bottom portion of the distillation column.

TABLE 1

Elements of Embodiments A-X

| Embodiment | Distillation Temp. Range (° C.) | | | Temp. Gradient Range (%) | | Distillation Pressure Range (mm Hg) | | Pressure Gradient Range (%) | |
|---|---|---|---|---|---|---|---|---|---|
| | 50-130 | 70-110 | 75-105 | 10-40 | 20-30 | 70-120 | 80-110 | 10-40 | 20-30 |
| A | X | | | X | | X | | X | |
| B | | X | | X | | X | | X | |
| C | | | X | X | | X | | X | |
| D | X | | | | X | X | | X | |
| E | | X | | | X | X | | X | |
| F | | | X | | X | X | | X | |
| G | X | | | X | | | X | X | |
| H | | X | | X | | | X | X | |
| I | | | X | X | | | X | X | |
| J | X | | | | X | | X | X | |
| K | | X | | | X | | X | X | |
| L | | | X | | X | | X | X | |
| M | X | | | X | | X | | | X |
| N | | X | | X | | X | | | X |
| O | | | X | X | | X | | | X |
| P | X | | | | X | X | | | X |
| Q | | X | | | X | X | | | X |
| R | | | X | | X | X | | | X |
| S | X | | | X | | | X | | X |
| T | | X | | X | | | X | | X |
| U | | | X | X | | | X | | X |
| V | X | | | | X | | X | | X |
| W | | X | | | X | | X | | X |
| X | | | X | | X | | X | | X |

In embodiments of the disclosure, the distilling occurs at the conditions of any one of Embodiments A-X, and the added oxygen gas is present in the distillation column liquid in an amount of at least 5 ppmw; about 5 ppmw; about 1 ppmw to about 100 ppmw; about 1 ppmw to about 75 ppmw; about 1 ppmw to about 50 ppmw; about 1 ppmw to about 20 ppmw; about 1 ppmw to about 15 ppmw; about 1 ppmw to about 10 ppmw; about 5 ppmw to about 100 ppmw; about 5 ppmw to about 75 ppmw; about 5 ppmw to about 50 ppmw; about 5 ppmw to about 20 ppmw; about 5 ppmw to about 15 ppmw; or about 5 ppmw to about 10 ppmw.

Vinyl Aromatic Monomers

In embodiments of the present disclosure, the vinyl aromatic monomer of the methods provided herein comprises styrene, α-methyl styrene, vinyl toluene, divinyl benzene, styrenesulfonic acid, or a combination thereof. In one embodiment, the vinyl aromatic monomer is styrene. In another embodiment, the vinyl aromatic monomer is α-methyl styrene. In a further embodiment, the vinyl aromatic monomer is vinyl toluene. In another embodiment, the vinyl aromatic monomer is divinyl benzene. In yet another embodiment, the vinyl aromatic monomer is styrenesulfonic acid. The distillation column liquid of the methods provided herein may include one or more of the vinyl aromatic monomers.

Other compounds may be present in the distillation column liquid. In embodiments, the vinyl aromatic monomer is part of a mixture that is or is present in the distillation column liquid. For example, the vinyl aromatic monomer may be styrene, and the styrene may be part of a styrene-containing mixture. The styrene-containing mixture may be a mixture obtained industrially, from which styrene can be isolated by distillation. One example of a styrene-containing mixture is a crude styrene, i.e. a crude mixture obtained in the production of styrene from ethylbenzene. The crude styrene may comprise, in addition to styrene and ethylbenzene, toluene, benzene, cumene, α-methylstyrene, or a combination thereof. In addition, crude styrene may further comprise, typically in an amount up to 3% by weight, e.g. from 0.5 to 1.2% by weight, based on styrene, constituents having a boiling point higher than that of styrene. These "higher boilers" may include, for example, stilbenes, styrene oligomers, styrene polymers, diphenylethane, and/or 2-phenylnaphthalene. Mixtures from which styrene can be recovered may have, for example, the following composition: 1% of benzene, 2% of toluene, 40% of ethylbenzene, 56% of styrene, and 1% of higher boilers, each by weight of the mixture.

Embodiments of the methods provided herein include the following:

Embodiment 1—A method of inhibiting polymerization of vinyl aromatic monomers, the method comprising distilling a vinyl aromatic monomer in a distillation column to form a vinyl aromatic monomer distillate, the distillation column including a distillation column liquid; removing the vinyl aromatic monomer distillate from the distillation column; combining the vinyl aromatic monomer distillate with 4-tert-butylcatechol (TBC) to form a treated distillate; and adding a reflux liquid comprising the treated distillate to the distillation column liquid of the distillation column; wherein an added oxygen gas is present in the distillation column liquid in an amount of at least 1 ppmw, based on the weight of the vinyl aromatic monomer.

Embodiment 2—The method of Embodiment 1, further comprising forming a vinyl aromatic monomer product and the reflux liquid from the treated distillate; directing the reflux liquid into the distillation column; and directing the vinyl aromatic monomer product to storage.

Embodiment 3—The method of Embodiment 1 or Embodiment 2, wherein the vinyl aromatic monomer distillate comprises TBC.

Embodiment 4—The method of any one of Embodiments 1-3, wherein the added oxygen gas is present in the distillation column liquid in an amount of at least 5 ppmw.

Embodiment 5—The method of any one of Embodiments 1-3, wherein the added oxygen gas is present in the distillation column liquid in an amount of about 5 ppmw.

Embodiment 6—The method of any one of Embodiments 1-3, wherein the added oxygen gas is present in the distillation column liquid in an amount of about 1 ppmw to about 100 ppmw.

Embodiment 7—The method of any one of Embodiments 1-3, wherein the added oxygen gas is present in the distillation column liquid in an amount of about 1 ppmw to about 75 ppmw.

Embodiment 8—The method of any one of Embodiments 1-3, wherein the added oxygen gas is present in the distillation column liquid in an amount of about 1 ppmw to about 50 ppmw.

Embodiment 9—The method of any one of Embodiments 1-3, wherein the added oxygen gas is present in the distillation column liquid in an amount of about 1 ppmw to about 20 ppmw.

Embodiment 10—The method of any one of Embodiments 1-3, wherein the added oxygen gas is present in the distillation column liquid in an amount of about 1 ppmw to about 15 ppmw.

Embodiment 11—The method of any one of Embodiments 1-3, wherein the added oxygen gas is present in the distillation column liquid in an amount of about 1 ppmw to about 10 ppmw.

Embodiment 12—The method of any one of Embodiments 1-11, wherein a concentration gradient of the added oxygen gas exists in the distillation column.

Embodiment 13—The method of any one of Embodiments 1-12, wherein a concentration of the added oxygen gas in the vinyl aromatic monomer of the distillation column liquid is greater than a concentration of the added oxygen gas in the vinyl aromatic monomer distillate.

Embodiment 14—The method of any one of Embodiments 1-13, wherein a concentration of the added oxygen gas in a bottom portion of the distillation column is greater than a concentration of the added oxygen gas in a top portion of the distillation column.

Embodiment 15—The method of any one of Embodiments 1-14, further comprising adding air to the distillation column with an air purge.

Embodiment 16—The method of Embodiment 15, wherein the air purge adds the air at a rate sufficient to maintain the at least 1 ppmw of the added oxygen gas in the distillation column liquid.

Embodiment 17—The method of any one of Embodiments 1-16, further comprising adding a gas to the distillation column with a gas purge, wherein the gas comprises oxygen gas and at least one inert gas.

Embodiment 18—The method of Embodiment 17, wherein the at least one inert gas comprises nitrogen, argon, or a combination thereof.

Embodiment 19—The method of Embodiment 17 or Embodiment 18, wherein the gas purge adds the gas at a rate sufficient to maintain the at least 1 ppmw of the added oxygen gas in the distillation column liquid.

Embodiment 20—The method of any one of Embodiments 15-19, wherein the distillation column comprises a boot, and the air purge and/or gas purge is connected to the boot.

Embodiment 21—The method of any one of Embodiments 15-20, wherein the air purge and/or gas purge adds the air and/or gas, respectively, to a bottom portion of the distillation column.

Embodiment 22—The method of any one of Embodiments 1-21, wherein the distilling occurs at a temperature of about 50° C. to about 130° C.

Embodiment 23—The method of any one of Embodiments 1-21, wherein the distilling occurs at a temperature of about 70° C. to about 110° C.

Embodiment 24—The method of any one of Embodiments 1-21, wherein the distilling occurs at a temperature of about 75° C. to about 105° C.

Embodiment 25—The method of any one of Embodiments 1-21, wherein the distilling occurs at a temperature of about 77° C. to about 101° C.

Embodiment 26—The method of any one of Embodiments 1-25, wherein a temperature gradient exists in the distillation column.

Embodiment 27—The method of any one of Embodiments 1-26, wherein an internal temperature (° C.) of a top portion of the distillation column is about 10% to about 40% less than an internal temperature (° C.) of a bottom portion of the distillation column.

Embodiment 28—The method of any one of Embodiments 1-26, wherein an internal temperature (° C.) of a top portion of the distillation column is about 20% to about 30% less than an internal temperature (° C.) of a bottom portion of the distillation column.

Embodiment 29—The method of any one of Embodiments 1-26, wherein an internal temperature of a top portion of the distillation column is about 70° C. to about 85° C., and an internal temperature of a bottom portion of the distillation column is about 90° C. to about 110° C.

Embodiment 30—The method of any one of Embodiments 1-26, wherein an internal temperature of a top portion of the distillation column is about 75° C. to about 80° C., and an internal temperature of a bottom portion of the distillation column is about 95° C. to about 105° C.

Embodiment 31—The method of any one of Embodiments 1-26, wherein an internal temperature of a top portion of the distillation column is about 77° C., and an internal temperature of a bottom portion of the distillation column is about 101° C.

Embodiment 32—The method of any one of Embodiments 1-31, wherein the distilling occurs at a pressure of about 70 mm Hg to about 120 mm Hg.

Embodiment 33—The method of any one of Embodiments 1-31, wherein the distilling occurs at a pressure of about 80 mm Hg to about 110 mm Hg.

Embodiment 34—The method of any one of Embodiments 1-33, wherein a pressure gradient exists in the distillation column.

Embodiment 35—The method of any one of Embodiments 1-34, wherein the distilling occurs at a temperature of about 50° C. to about 130° C. and at a pressure of about 70 mm Hg to about 120 mm Hg.

Embodiment 36—The method of any one of Embodiments 1-34, wherein the distilling occurs at a temperature of about 50° C. to about 130° C. and at a pressure of about 80 mm Hg to about 110 mm Hg.

Embodiment 37—The method of any one of Embodiments 1-34, wherein the distilling occurs at a temperature of about 70° C. to about 110° C. and at a pressure of about 70 mm Hg to about 120 mm Hg.

Embodiment 38—The method of any one of Embodiments 1-34, wherein the distilling occurs at a temperature of about 70° C. to about 110° C. and at a pressure of about 80 mm Hg to about 110 mm Hg.

Embodiment 39—The method of any one of Embodiments 1-34, wherein the distilling occurs at a temperature of about 75° C. to about 105° C. and at a pressure of about 70 mm Hg to about 120 mm Hg.

Embodiment 40—The method of any one of Embodiments 1-34, wherein the distilling occurs at a temperature of about 75° C. to about 105° C. and at a pressure of about 80 mm Hg to about 110 mm Hg.

Embodiment 41—The method of any one of Embodiments 1-40, wherein an internal pressure of a top portion (mm Hg) of the distillation column is about 10% to about 40% less than an internal pressure of a bottom portion (mm Hg) of the distillation column.

Embodiment 42—The method of any one of Embodiments 1-40, wherein an internal pressure of a top portion (mm Hg) of the distillation column is about 20% to about 35% less than an internal pressure of a bottom portion (mm Hg) of the distillation column.

Embodiment 43—The method of any one of Embodiments 1-40, wherein an internal pressure of a top portion of the distillation column is about 70 mm Hg to about 90 mm Hg, and an internal pressure of a bottom portion of the distillation column is about 100 mm Hg to about 120 mm Hg.

Embodiment 44—The method of any one of Embodiments 1-40, wherein an internal pressure of a top portion of the distillation column is about 75 mm Hg to about 85 mm Hg, and an internal pressure of a bottom portion of the distillation column is about 105 mm Hg to about 115 mm Hg.

Embodiment 45—The method of any one of Embodiments 1-40, wherein an internal pressure of a top portion of the distillation column is about 80 mm Hg, and an internal pressure of a bottom portion of the distillation column is about 110 mm Hg.

Embodiment 46—The method of any one of Embodiments 1-45, wherein the vinyl aromatic monomer is styrene.

Embodiment 47—The method of any one of Embodiments 1-45, wherein the vinyl aromatic monomer is α-methyl styrene.

Embodiment 48—The method of any one of Embodiments 1-45, wherein the vinyl aromatic monomer is vinyl toluene.

Embodiment 49—The method of any one of Embodiments 1-45, wherein the vinyl aromatic monomer is divinyl benzene.

Embodiment 50—The method of any one of Embodiments 1-45, wherein the vinyl aromatic monomer is styrenesulfonic acid.

Embodiment 51—The method of any one of Embodiments 1-50, wherein the vinyl aromatic monomer comprises styrene, α-methyl styrene, vinyl toluene, divinyl benzene, styrenesulfonic acid, or a combination thereof.

For any particular compound disclosed herein, any general structure presented also encompasses all conformational isomers, regioisomers, and stereoisomers that may arise from a particular set of substitutents. Thus, the general structure also encompasses all enantiomers, diastereomers, and other optical isomers whether in enantiomeric or racemic forms, as well as mixtures of stereoisomers, as the context requires.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—TBC Activity

A test was performed to determine the polymerization inhibiting activity of TBC in styrene. Three samples were heated in a vessel for up to 110 minutes at 120° C. (248° F.). The first sample included only styrene, the second sample included styrene and TBC, but no oxygen gas, and the third sample included styrene, TBC, and oxygen gas. The dissolved oxygen concentration was estimated to be about 11 ppm, based on literature data extrapolated to 120° C. (248° F.) (see, e.g., Cunningham, M. F. et al. "*Measuring the effects of dissolved oxygen in styrene emulsion polymerization,*" POLYMER, 2000, 41, 5385-5392). In other words, at the start of the test, the styrene was in equilibrium with air, and at a temperature of about 25° C.; therefore, the initial oxygen concentration was estimated to be about 50 ppmW. By extrapolation, it was estimated that the oxygen concentration was about 11 ppmW during the experiment, when the temperature was held at 120° C.

FIG. 1 depicts the weight percentage of polystyrene, based on the weight of each sample, produced as each sample was heated.

As shown at FIG. 1, the weight percentage of polystyrene in samples 1 and 2 increased almost identically, despite the fact that sample 2 included TBC. The similarity of these data indicated the important role of oxygen gas. The presence of oxygen gas ensures and/or increases the polymerization inhibition activity of TBC, because, as shown at FIG. 1, the weight percentage of polystyrene in the third sample remained well-below 1 weight % until the sample had been heated for nearly 90 minutes.

The data shown in FIG. 1 generally indicates that the methods provided herein, which require the presence of a minimum amount of oxygen gas in the distillation column, ensure and/or increase the polymerization inhibition activity of TBC in the distillation column.

We claim:

1. A method of inhibiting polymerization of vinyl aromatic monomers, the method comprising:
   distilling a vinyl aromatic monomer in a distillation column to form a vinyl aromatic monomer distillate, the distillation column including a distillation column liquid;
   removing the vinyl aromatic monomer distillate from the distillation column;
   combining the vinyl aromatic monomer distillate with 4-tert-butylcatechol (TBC) to form a treated distillate; and
   adding a reflux liquid comprising the treated distillate to the distillation column liquid of the distillation column;
   wherein an added oxygen gas is present in the distillation column liquid in an amount of at least 1 ppmw and less than 100 ppmw, based on the weight of the vinyl aromatic monomer.

2. The method of claim 1, further comprising forming a vinyl aromatic monomer product and the reflux liquid from the treated distillate; directing the reflux liquid into the distillation column; and directing the vinyl aromatic monomer product to storage.

3. The method of claim 1, wherein the vinyl aromatic monomer distillate comprises TBC.

4. The method of claim 1, wherein the added oxygen gas is present in the distillation column liquid in an amount of at least 5 ppmw.

5. The method of claim 1, wherein the added oxygen gas is present in the distillation column liquid in an amount of about 5 ppmw.

6. The method of claim 1, further comprising adding air to the distillation column with an air purge.

7. The method of claim 6, wherein the air purge adds the air at a rate sufficient to maintain the at least 1 ppmw of the added oxygen gas in the distillation column liquid.

8. The method of claim 1, further comprising adding a gas to the distillation column with a gas purge, wherein the gas comprises oxygen gas and at least one inert gas.

9. The method of claim 1, wherein the distilling occurs at a temperature of about 50° C. to about 130° C.

10. The method of claim 1, wherein the distilling occurs at a temperature of about 70° C. to about 110° C.

11. The method of claim 1, wherein an internal temperature (° C.) of a top portion of the distillation column is about 10% to about 40% less than an internal temperature (° C.) of a bottom portion of the distillation column.

12. The method of claim 1, wherein an internal temperature (° C.) of a top portion of the distillation column is about 20% to about 30% less than an internal temperature (° C.) of a bottom portion of the distillation column.

13. The method of claim 1, wherein an internal temperature of a top portion of the distillation column is about 70° C. to about 85° C., and an internal temperature of a bottom portion of the distillation column is about 90° C. to about 110° C.

14. The method of claim 1, wherein an internal temperature of a top portion of the distillation column is about 75° C. to about 80° C., and an internal temperature of a bottom portion of the distillation column is about 95° C. to about 105° C.

15. The method of claim 1, wherein the distilling occurs at a pressure of about 70 mm Hg to about 120 mm Hg.

16. The method of claim 1, wherein the distilling occurs at a pressure of about 80 mm Hg to about 110 mm Hg.

17. The method of claim 1, wherein a pressure gradient exists in the distillation column.

18. The method of claim 1, wherein the vinyl aromatic monomer comprises styrene, α-methyl styrene, vinyl toluene, divinyl benzene, styrenesulfonic acid, or a combination thereof.

19. The method of claim 1, wherein the vinyl aromatic monomer comprises styrene.

20. The method of claim 1, wherein the added oxygen gas is present in the distillation column liquid in an amount of about 1 ppmw to about 75 ppmw.

* * * * *